(12) United States Patent
Ollmar et al.

(10) Patent No.: US 7,050,847 B2
(45) Date of Patent: May 23, 2006

(54) NON-INVASIVE IN VIVO DETERMINATION OF BODY FLUID PARAMETER

(76) Inventors: Stig Ollmar, Hällebergsvägen 19, Huddinge (SE) SE-14141; Peter Åberg, Röntgenvägen 5, våning 8, rum 8687, Huddinge (SE) SE-14152; Alan Lorne Perlmutter, 3 Sprucedale Court, London, Ontario (CA) N5X 2N9

( * ) Notice: Subject to any disclaimer, the term of this patent is extended or adjusted under 35 U.S.C. 154(b) by 323 days.

(21) Appl. No.: 10/396,709

(22) Filed: Mar. 26, 2003

(65) Prior Publication Data

US 2003/0220581 A1    Nov. 27, 2003

Related U.S. Application Data

(60) Provisional application No. 60/367,196, filed on Mar. 26, 2002, provisional application No. 60/417,561, filed on Oct. 11, 2002.

(51) Int. Cl.
*A61B 5/05* (2006.01)

(52) U.S. Cl. ........................ 600/547; 600/365

(58) Field of Classification Search ................ 600/365, 600/547
See application file for complete search history.

(56) References Cited

U.S. PATENT DOCUMENTS

| | | | |
|---|---|---|---|
| 4,798,955 A * | 1/1989 | Rosenthal .................... 600/310 |
| 5,028,787 A * | 7/1991 | Rosenthal et al. ..... 250/339.12 |
| 5,036,861 A | 8/1991 | Sembrowich et al. |
| 5,115,133 A | 5/1992 | Knudson |
| 5,146,091 A | 9/1992 | Knudson |
| 5,179,951 A | 1/1993 | Knudson |
| 5,222,496 A | 6/1993 | Clarke et al. |
| 5,353,802 A | 10/1994 | Ollmar |
| 5,433,197 A | 7/1995 | Stark |
| 5,508,203 A | 4/1996 | Fuller et al. |
| 5,792,668 A * | 8/1998 | Fuller et al. ................. 436/149 |

(Continued)

FOREIGN PATENT DOCUMENTS

WO    WO 01/26538    4/1992

(Continued)

OTHER PUBLICATIONS

Andersson, C. et al. "The N-way toolbox for MATLAB," Chemometrics Intelligent Laboratory Systems, vol. 52, issue 1, 2000, pp. 1 to 4.

(Continued)

*Primary Examiner*—Eric F. Winakur
(74) *Attorney, Agent, or Firm*—Blake, Cassels & Graydon LLP; Louise Foong; Mark Penner

(57) ABSTRACT

A non-invasive method of monitoring a biological parameter concerning a bodily fluid of a subject, e.g., blood glucose of a human subject. The method includes: placing an electrode against a site of the skin of the subject; measuring impedance of the skin and determining the parameter therefrom; and using substantially the same site in another determination. Another non-invasive monitoring method includes: exposing a skin site to an aqueous salt solution for a pre-determined first period of time; removing excess of the solution from the site; measuring impedance at the site; exposing the site to the solution for a pre-determined second period of time and repeating the removing and measuring steps. It is determined whether the impedance measured falls within a pre-determined range. The latter exposure and removal steps are repeated, if necessary, until two consecutive impedance measurements within the pre-determined range are obtained.

17 Claims, 12 Drawing Sheets

U.S. PATENT DOCUMENTS

| | | | |
|---|---|---|---|
| 5,890,489 A | | 4/1999 | Elden |
| 6,334,856 B1 | | 1/2002 | Allen et al. |
| 6,339,722 B1 | | 1/2002 | Heethaar et al. |
| 6,517,482 B1 | | 2/2003 | Elden et al. |
| 6,631,282 B1 | * | 10/2003 | Rule et al. .................. 600/344 |
| 6,841,389 B1 | * | 1/2005 | Novikov et al. .............. 436/95 |

FOREIGN PATENT DOCUMENTS

| | | |
|---|---|---|
| WO | WO 92/06634 | 4/1992 |
| WO | WO 95/04496 | 2/1995 |
| WO | WO 98/04190 | 2/1998 |
| WO | WO 99/39627 | 8/1999 |
| WO | WO 01/52731 | 7/2001 |

OTHER PUBLICATIONS

Lindholm-Sethson, B. et al. "Interaction with a phospholipid monolayer on a mercury electrode. Multivariate analysis of impedance data." Analytica Chimica ACTA, vol. 446, 2001, pp. 121 to 131.

Bro, R. et al. "A fast least squares algorithm for separating trilinear mixtures." Proceedings of ICA99—International Workshop on Independent Component Analysis and Blind Signal Separation, Jan. 11-15, 1999, Aussois, France, pp. 289-294.

Cornish, B.H. et al. "Effect of temperature and sweating on bioimpedance measurements" Applications of Radioactive Isotopes, vol. 49, issues 5 to 6, May to Jun. 1998, pp. 475 to 476.

Nicander, I. et al. "Electrical impedance measurements at different skin sites related to seasonal variations." Skin Research Technology, vol. 6, 2000, pp. 81 to 86.

Robinson, M.K. "Intra-individual variations in acute and cumulative skin irritation responses." Contact Dermatitis, vol. 45, issue 2, Aug. 2001, pp. 75-83.

Griss et al. "Micromachined electrodes for biopotential measurements." Journal of Microelectromechanical Systems, vol. 10, issue 1, Mar. 2001, pp. 10 to 16.

Emtestam, I. et al. "Electrical impedance ofnodular basal cell carcinoma: a pilot study." Dermatology, vol. 197, 1998, pp. 313 to 316.

Kapoor, S. "Bioelectric impedance techniques for clinical detection of skin cancer," Thesis, University of Missouri-Rolla, 2001.

Ollmar, S. et al. "Electrical impedance for estimation of irritation in oral mucosa and skin." Medical Progress Through Technology, vol. 21, No. 1, Feb. 1, 1995, pp. 29 to 37.

Berg, P., et al.: "Variation of skin properties within human forearms demonstrated by non-invasive detection and multiway analysis", Skin Research and Technology, vol. 8, issue 3, Aug. 2002, pp. 194 to 201.

Björnberg, A. "Skin reactions to primary irritants in patients with hand eczema: an investigation with matched controls." Thesis. Sahlgrenska Sjukhuset, Gothenburg, Sweden, 1968.

Nicander, I., et al. "Electrial impedance and other physical parameters as relate to lipid content of human stratum corneum." Skin Research and Technology, vol. 4, 1998, pp. 213-221.

Nilsson, G.E. "On the measurement of evaporative water loss. Methods and clinical applications." Thesis. Linkping Medical University, Linkping, Sweden, 1977.

Pinnagoda, J. et al. "Guidelines for transepidermal water loss (TEWL) measurement: A report from the Standardization Group of the European Society of Contact Dermatitis." Contact Dermatitis, vol. 22, 1990, pp. 164 to 178.

Rodrigues, L. et al. "Basal transepidermal water loss: right/left forearm difference and motoric dominance," Skin Research Technology, vol. 4, 1998, pp. 135 to 137.

Van Der Valk, P.G. et al. "Potential for irritation increases from the wrist to the cubital fossa," British Journal of Dermatology, vol. 121, issue 6, Dec. 1989, pp. 709 to 712.

Tur, E. et al. "Spatial variability of vasodilatation in human forearm skin." British Journal of Dermatology, vol. 113, issue 2, Aug. 1985, pp. 197 to 203.

Wold, S. et al. "Principal component analysis." Chemometrics Intelligent Laboratory Systems, vol. 2, 1987, pp. 37 to 52.

Geladi, P. et al. "Three-way modelling of a batch organic synthesis process monitored by near infrared spectroscopy." Journal of Near Infrared Spectrscopy, vol. 9, 2001, pp. 1 to 9.

Bro, R. "Parafac: Tutorial and applications." Chemometrics Intelligent Laboratory Systems, vol. 38, 1994, pp. 149-171.

Harshman, R.A. "Foundations of the Parafac procedure: Model and conditions for an 'explanatory' multi-mode factor analysis." UCLA Working Papers in Phonetics, vol. 16, 1970, pp. 1 to 84.

Carrol, J.D. "Analysis of individual differences in multidimensional scaling via an N-way generalization of the Eckart-Youngdecomposition." PSYCOMETRIKA, vol. 35, 1970, pp. 282 to 319.

Geladi, P. "Analysis of multi-way (multi-mode) data." Chemometrics Intelligent Laboratory Systems, vol. 7, 1989, pp. 11 to 30.

Smilde, A. "Three-way analyses. Problems and prospects." Chemometrics Intelligent Laboratory Systems, vol. 14, 1992, pp. 143 to 157.

"Special Issue: Multiway Analysis" Journal of Chemometrics Eds. Andersson, C. et al., vol. 14, 2000.

Foster, K. "Dielectric properties of tissues and biological materials: a critical review." Critical Reviews in Biomedical Engineering, vol. 17, 1989, pp. 25 to 104.

Ollmar, S. "Making electronic biopsies into a viable future for non-invasive diagnostics with electrical impedance." Medical and Biological Engineering and Computing, vol. 37, supplement 2, 1999, pp. 116 to 117.

Ollmar, S. "Methods of information extraction from impedance spectra of biological tissue, in particular skin and oral mucosa—a critical review and suggestions for the future." Bioelectrochemistry & Bioenergetics, vol. 45, 1998, pp. 157 to 160.

Åberg, P. et al. "Multivariate regression model of normal and chemically irritates skin shows predictive ability." Proceedings of the European Molecular Biology Conference, 2001, Istanbul, Turkey, Oct. 25 to 28, 2001, ISBN 0-7803-7213-1.

Lindholdm-Sethson B. et al. "Multivariage analysis of skin impedance data in long-term type 1 diabetic patient." Chemometrics Intelligent Laboratory Systems, vol. 44, 1998, pp. 381-394.

Nicander, I. "Electrical impedance related to experimentally induced changes of human skin and oral mucosa." Thesis, Karolinska Institutet, Stockholm, Sweden, 1998.

* cited by examiner

Figure 11a
Figure 11b
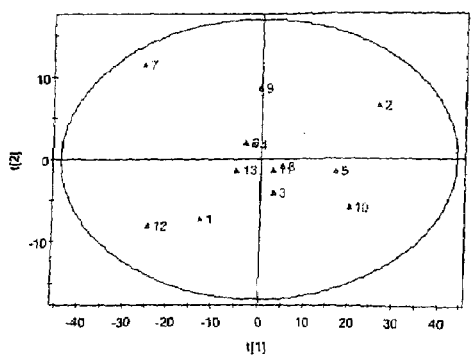
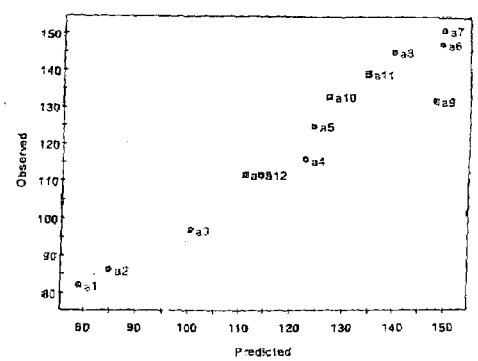
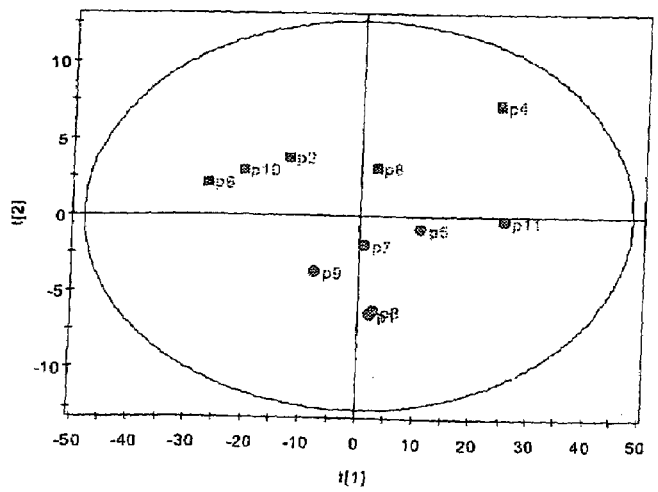
Figure 12

NON-INVASIVE IN VIVO DETERMINATION OF BODY FLUID PARAMETER

This application claims priority from U.S. Provisional Patent Application Ser. Nos. 60/367,196, filed Mar. 26, 2002, and 60/417,561, filed Oct. 11, 2002, the entire contents of which applications are incorporated herein by reference.

FIELD OF THE INVENTION

This invention relates to a method of measuring impedance for the in vivo non-invasive determination of a biological parameter concerning a bodily fluid of a mammal. A particular aspect of the invention relates to measuring the impedance repetitively at the same site for determining a blood glucose level, to an apparatus for use in such measurements, etc. In another aspect, the invention involves a combination of multiple treatment steps of the skin site at which the impedance measurements are taken multiple impedance measurements in the determination.

BACKGROUND OF THE INVENTION

Non-invasive measurement of skin impedance is described in the patent literature, for example, in U.S. Pat. No. 5,890,489 which issued on Apr. 6, 1999, and international patent application No. PCT/US 98/02037 published initially on Aug. 12, 1999 under WO 99/39627, and again as U.S. Pat. No. 6,517,482 on Feb. 11, 2003. These documents describe the use of skin impedance measurements in determining the level of a subject's blood glucose.

Any understanding of factors that influence the variability of impedance measurements in determining blood glucose levels that leads to an improvement in the reliability of such measurements is of inherent value, particularly to diabetics that need to continually monitor their blood glucose levels. It is well known that there is a need for a person to be able to quickly and conveniently make such a determination. There is evidence that increased frequency of blood glucose determination, which can lead to a finer level of control of blood glucose, can lead to an improved outcome, especially over a period of many years. With improved convenience and economics of blood glucose determination could thus enable a diabetic to improve outcome through increased frequency of monitoring of blood glucose levels.

In dermatology experiments and investigations, where many sites are used, the skin properties of the sites are often considered to be identical from one site to the next, or at least nearly so. This is evidently not always true. In fact, the properties of human skin can vary from place to place on the body (1). The properties also vary locally on body parts. Nicander et al. (2) measured skin impedance and transepidermal water loss (TEWL) (3, 4) at three locations on forearms: one close to the crook of the arm, one close to the wrist, and one in between, and found differences between the three sites. Moreover, Rodrigues and Pereira (5) showed that TEWL close to the crook of the arm and close to the wrist is higher than in between, where the TEWL is relatively constant. They also found that TEWL of the most active arm is higher than the accessory.

Since the baseline properties of the forearms vary locally, the skin of the forearms reacts differently from place to place to external stimuli. Van der Valk and Maibach (6) found significant irritation patterns along volar forearms and concluded that the potential irritation varies gradually between the wrist and crook of the arm. Similar results were demonstrated by Tur et al. (7). They studied the photoplethysmographic response of a drug on various locations at the arms and found differences between upper and lower part of the volar forearms, but not between right and left arm, or between inner and outer sides of the arms.

SUMMARY OF THE INVENTION

Properties of the skin of the volar forearms were investigated using two independent non-invasive detection techniques: a TEWL meter and a depth selective skin impedance spectrometer. The TEWL meter gives a numerical value of the amount water that evaporates from 1 m² per hour ($g\ m^{-2}h^{-1}$).

A reading from the depth selective skin impedance spectrometer gives an impedance matrix with 5 depth settings times 31 frequencies, where the impedance at each frequency is a pair of numbers, i.e. the magnitude and phase. All elements in the impedance matrix are highly correlated. Hence, a collection of impedance spectra readings will produce a three-way array (readings×depth settings×frequencies).

Analysis of variance (ANOVA) is used for layouts with one response. The ANOVA tests the response for statistical significance. When a few responses are produced, multivariate analysis of variance (MANOVA) (8,9) of the data can provide relevant information, but too many response variables make the conclusions unclear. A better approach is to extract the latent information using projection techniques. This gives a data reduction that allows MANOVA testing. A commonly used projection technique for matrices is principal component analysis (PCA) (10). Related data reduction techniques for multi-way arrays are Tucker 3, and parallel factor analysis (PARAFAC) (11–18).

Electrical impedance of biological tissues varies with frequency. Different frequency intervals contain different types of information. For example, impedance at lower frequencies is influenced by the extra-cellular environment and impedance at higher frequencies by the structure and shape of the cells and the cell membranes (19). In impedance spectra this information is diffusely spread and overlapped in the whole frequency range.

In order to capture most of the information and to simplify the numerical analysis of impedance spectra ollmar and Nicander (20) used parameterisation from impedance spectra at two frequencies. This approach provides sufficient information for many applications, e.g. skin irritations and contact allergy reactions. When subtle skin responses and phenomena are analysed, however, it is better to use all information from the whole impedance spectra (21, 22) using, for example, projection techniques (23, 24).

The results described herein establish a non-invasive method of monitoring a biological parameter concerning a bodily fluid of a mammal. The method includes:

(i) placing an electrode against a site of the skin of the mammal;

(ii) measuring impedance of the skin and determining said parameter therefrom; and (iii) after a period of time, repeating steps (i) and (ii), wherein during each placing step, said site is substantially the same site.

The period of time in step (iii) of the method would most often be the period a person would typically take between measurements in monitoring their blood glucose. This varies from person to person depending upon their particular condition. The period could thus be between ½ hour and 48 hours, or 1 hour and 48 hours, or between 1 hour and 36 hours, or between 1 hour and 24 hours, or between 1 hour and 22 hours, or between 1 hour and 20 hours, or between 1 hour and 18 hours, or between 1 hour and 16 hours, or between 1 hour and 14 hours, or between 1 hour and 12 hours, or between 1 hour and 10 hours, or between 1 hour and 8 hours, or between 1 hour and 7 hours, or between 1 hour and 6 hours, or between 1 hour and 5 hours, or between 1 hour and 4 hours, or between 1 hour and 3 hours, or between 1 and 2 hours.

Towards the end of using substantially the same site from measurement to measurement, the electrode can be marked in such a way that it is convenient for the user to repeatedly place it on the skin in the same way. The electrode can thus have a reference point which abuts a first point of the skin when the electrode is placed against the skin, and during said repeating of step (i) a second said point of the skin is within a distance of 1 cm of the first point of the skin. In other words, first and second points are considered to be substantially the same site of the skin if they are within 1 cm of each other.

The method can additionally, or alternatively, involve the use of an indexing device, separate from the electrode, for locating the skin site from measurement to measurement. In such an embodiment, the method thus involves, prior to step (i), locating the indexing device adjacent the skin of the subject wherein said site of step (i) is determined by its location with respect to a predetermined position of the device.

In a particularly preferred embodiment, the method is conducted on a human, and the site can be located on the volar forearm, much as described in the experiments described below, if this is convenient.

Most often, the subject is concerned with monitoring their blood glucose level by means of the impedance measurement of the method.

Preferably, a center point of the site in step (i) is spaced no more than the diameter of the electrode in contact with the skin from the center point of the site when step (i) is repeated, more preferably, no more than the radius of the electrode, more preferably no more than the radius/2 of the electrode. "Radius" of course implies that the skin contact region(s) of the electrode lies on circle, but analogously, the maximum cross dimension of a contact region(s) lying on a square, rectangle, or other shape could be used in determining the center point from measurement to measurement in maintaining substantially the same site.

The center point of a said site in step (i) is preferably spaced no more than 3 cm (more preferably, no more than 2.5 cm, more preferably 2 cm, more preferably 1.5 cm, more preferably 1 cm, and even more preferably 0.5 cm) from the center point of a said site when step (i) is repeated.

The measurement site can be marked on the skin to ensure that substantially the same site is used from measurement to measurement. A permanent, or semi-permanent tatoo could be used. Further the indexing device could be used for marking a semi-permanent tatoo from time to time, to ensure that such a tatoo is reliably located at substantially the same site from marking to marking.

In another embodiment, the invention includes a method of calibrating an impedance measuring device for use with a mammalian subject. The method includes:
(i) locating an indexing tool in a predetermined position against the skin of the mammal;
(ii) placing a probe of the device against the skin at a predetermined location with respect to the tool;
(iii) measuring impedance of the skin;
(iv) measuring a biological parameter concerning a bodily fluid of a mammal; and
(v) correlating the measurements of steps (iii) and (iv).

The method includes an apparatus for measuring a biological parameter concerning a bodily fluid of a mammal. The apparatus includes an indexing tool for placement in predetermined position against the skin of the mammal, the tool including an indicator for locating a probe with respect thereto against the skin of the mammal.

The apparatus can further include an impedance measuring device having the probe.

The apparatus is preferably accompanied by a set of instructions for use of the apparatus according to a method of the invention as described above.

In another aspect, the invention is a method for non-invasively monitoring a component in a body fluid of a subject that includes:
(i) exposing a skin site of the subject at which a measurement is to be made to an aqueous salt solution for a pre-determined first period of time;
(ii) (a) removing excess of the solution from the site; (b) measuring impedance at the site;
(iii) exposing the site to the solution for a pre-determined second period of time and repeating step (ii);
(iv) determining whether the impedance measured in step (iii) falls within a pre-determined range;
(v) repeating steps (iii) and (iv) as necessary until the impedance measured in step (iii) falls within the pre-determined range; and
(vi) determining the amount of the component in the fluid based upon the impedance measured in step (v).

One can thus appreciate that according to this aspect, reliability of blood glucose determinations of a subject, from determination to determination, increases by this method which involves repeatedly exposing the measurement site to a salt solution, and measuring impedance after each exposure.

The range of step (iv) can be empirically determined for the subject, the empirical determination being based on impedance measurements and a second type of measurement in which the amount of component present is determined for a sample of the body fluid obtained from the subject (e.g., the use of the "Elite(™) Glucometer" described below.

Preferably, steps (iii) and (iv) are repeated at least until the impedance measured in step (iii) falls with the pre-determined range for two consecutive of the impedance measurements.

The step of determining the amount of the component can be based on an average of the at least two consecutive impedance measurements.

Preferably, as in the exemplified embodiment, the first period is greater than said second period.

The first period is preferably at least about 40 seconds.

Preferably, the second period is less than about 20 seconds. More preferably, the second period is less than about 15 seconds.

In the disclosed embodiment, described in greater detail below, the second period is about 10 seconds.

Preferably, The first period is less than about 60 seconds, or less than about 50 seconds, or as described in the exemplified embodiment, the first period can be about 40 seconds.

The salt solution can include an inorganic salt compatible with human skin, and preferably it would include a saline solution, typically between 0.5 and 0.15% (wt/total volume, e.g. a 15% solution is 15 gm NaCl brought to a total volume of 100 ml through addition of distilled water). The solution could also be somewhere between 0.6 and 0.13%, or between 0.7 and 0.11%, or it could be about 0.9%, as in the exemplified embodiment.

The method can also include, in step (ii) (b), measuring skin impedance using and an electrode in direct contact with (as by abutment therewith) the skin site. The impedance is preferably measured at a plurality of frequencies.

BRIEF DESCRIPTION OF THE DRAWINGS

Reference is made to the accompanying drawings, which are briefly described as follows:

FIG. 11a. Scatter plot Person A's impedance measurements.

FIG. 11b. Plot of Person A's directly measured blood glucose versus level as predicted from impedance measurement: observed (●); predicted (■).

FIG. 12. Scatter plot Person B's impedance measurements: left arm (●), right arm (■).

DESCRIPTION OF DETAILED EMBODIMENTS

Methods

Clinical

Figure 1:
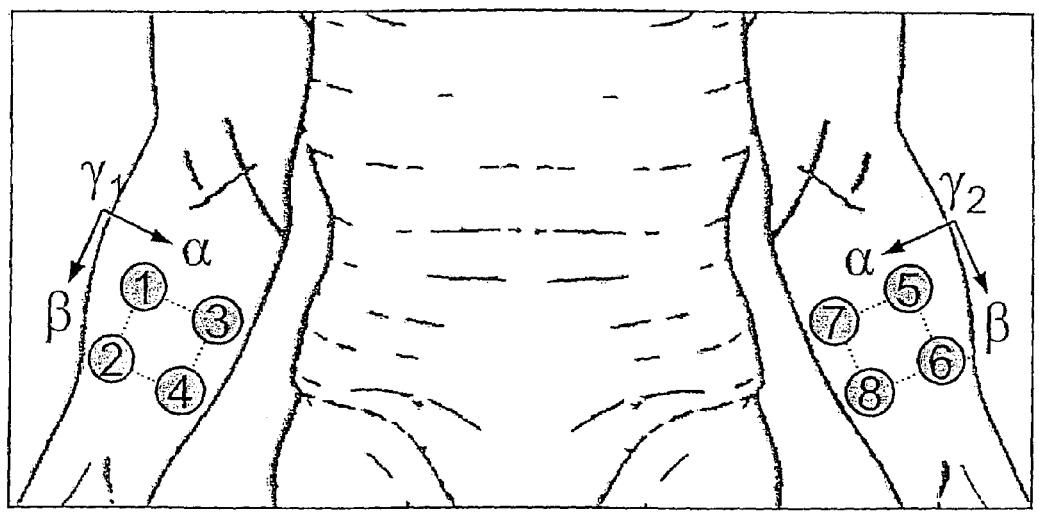
FIG. 1. Locations of the eight sites where the skin impedance and TEWL was measured. The three directions, α, β, and γ, defined in table 1, are marked.

Skin impedance was collected from eight sites on right and left forearms of 27 healthy Caucasian volunteers (12 females and 15 males) according to standard operating procedures (25) using an electrical impedance spectrometer (SciBase AB, Huddinge, Sweden). Magnitude and phase angle of the skin impedance spectra were measured at 31 logarithmically distributed frequencies from 1 kHz to 1 MHz at five depth settings. TEWL was measured on 27 healthy volunteers (13 females and 14 males) using an Evaporimeter EP1 (Servomed, Kinna, Sweden) on the same sites using standard operating procedures (4, 25). The sites were located approximately 40 to 50 mm apart close to the centre of the volar forearms. The locations of the sites can be described by three directions, α, β, and γ, at two levels. The sites are marked in FIG. 1, and the directions are described in detail in Table 1.

TABLE 1

The directions describing the locations of the sites.

| Direction | Description | Sites of level 1 | Sites of level 2 |
|---|---|---|---|
| α | Outer and inner side | 1, 2, 5 and 6 | 3, 4, 7, and 8 |
| β | Upper and lower side | 1, 3, 5, and 7 | 2, 4, 6, and 8 |
| γ | Right and left arm | 1, 2, 3, and 4 | 5, 6, 7, and 8 |

Numerical

Electrical Impedance and Parameterisation

Impedance, Z, is a complex unit, according to [1], where R is the resistance (Ohm), X the reactance (Ohm), and i is given by [2].

$$Z = R + iX \quad [1]$$

$$i = \sqrt{-1} \quad [2]$$

The impedance can be expressed in polar coordinates, given by [3–5], using the magnitude, |Z| (Ohm), and phase angle, θ (deg).

$$Z = |Z|e^{i\theta} \quad [3]$$

$$|Z| = (R^2 + X^2)^{0.5} \quad [4]$$

$$\theta = \tan^{-1}(X/R) \quad [5]$$

The four indices, magnitude index (MIX), phase index (PIX), real part index (RIX), and imaginary part index (IMIX), introduced by Ollmar and Nicander (20) are given by [6–9].

$$MIX = |Z_{20\ kHz}|/|Z_{500\ kHz}| \quad [6]$$

$$PIX = \theta_{20\ kHz} - \theta_{500\ kHz} \quad [7]$$

$$RIX = R_{20\ kHz}/|Z_{500\ kHz}| \quad [8]$$

$$IMIX = X_{20\ kHz}/|Z_{500\ kHz}| \quad [9]$$

The purpose of the parameterisation is to reduce the number of frequencies and to convert the complex valued impedance to real numbers, which simplifies the classical statistical analysis. The most powerful parameterisation in most applications is the magnitude index. All four indices were used in the data analysis, but only MIX values are presented here.

Parallel Factor Analysis

The basic idea of PARAFAC, and other similar decomposition tools, is to concentrate the information from the data to fewer variables using projections. For a typical three-way data array, X (I×J×K), with three modes, a number of PARAFAC components, R, are found that satisfy equation [10].

$$x_{ijk} = \sum_{r=1}^{R} a_{ir} b_{jr} c_{kf} + e_{ijk} \quad [10]$$

$a_{ir}$, $b_{jr}$, and $c_{kr}$ are typical elements of the loadings of the three modes: $a_r$, $b_r$, and $C_r$, respectively. The loadings describe the relation between the variables in and between each mode. $e_{ijk}$ is a typical element of the residual array E. Structure of a three-way two component PARAFAC model is visualized in FIG. 2.

Figure 2:
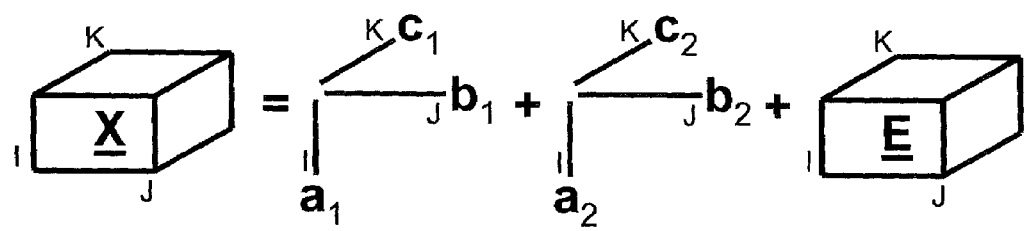
FIG. 2. PARAFAC decomposition of a three-way array X to two PARAFAC components.

PARAFAC models have important properties. They are parsimonious and therefore they require fewer parameters than most competing models and thereby avoiding overfitting. They also give separate loadings for each mode, as seen in FIG. 2, allowing a simple interpretation of all the modes by line or scatter plots. Methods working on matrices, such as PCA, would require reorganizing the three-way array to a matrix and give interpretation difficulties.

PARAFAC decompositions of multi-frequency skin impedance spectra were calculated using the PLS-toolbox (Eigenvector Research Inc., Manson, Wash., USA) and the N-way toolbox (26) in MATLAB environment (Mathworks Inc., Natick, Mass., USA). Three-way ANOVA's of magnitude index and TEWL were calculated using the general linear model for repeated measures in the SPSS software package (SPSS Inc., Chicago, Ill., USA).

Results

Figure 3:
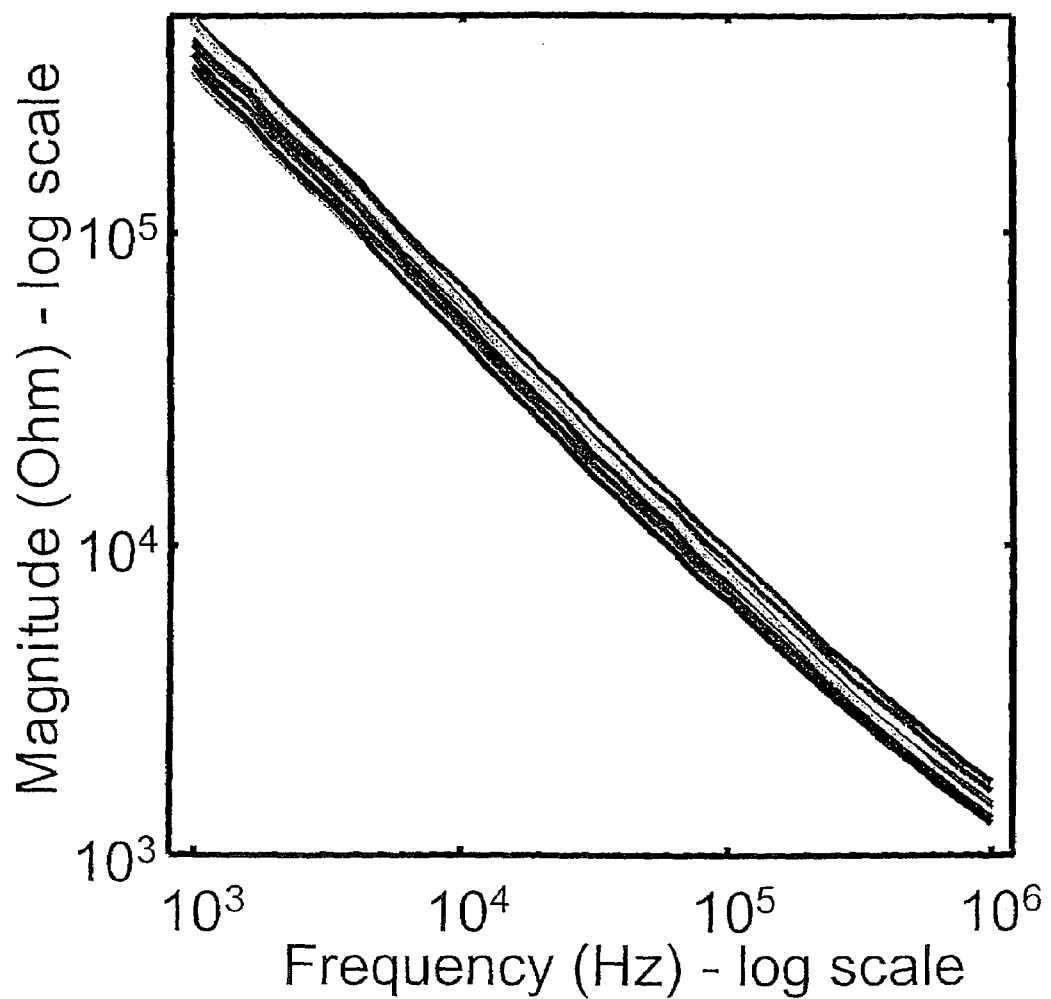
FIG. 3. Measured magnitude at 31 frequencies at eight sites for one person at depth setting number three.
Figure 4:
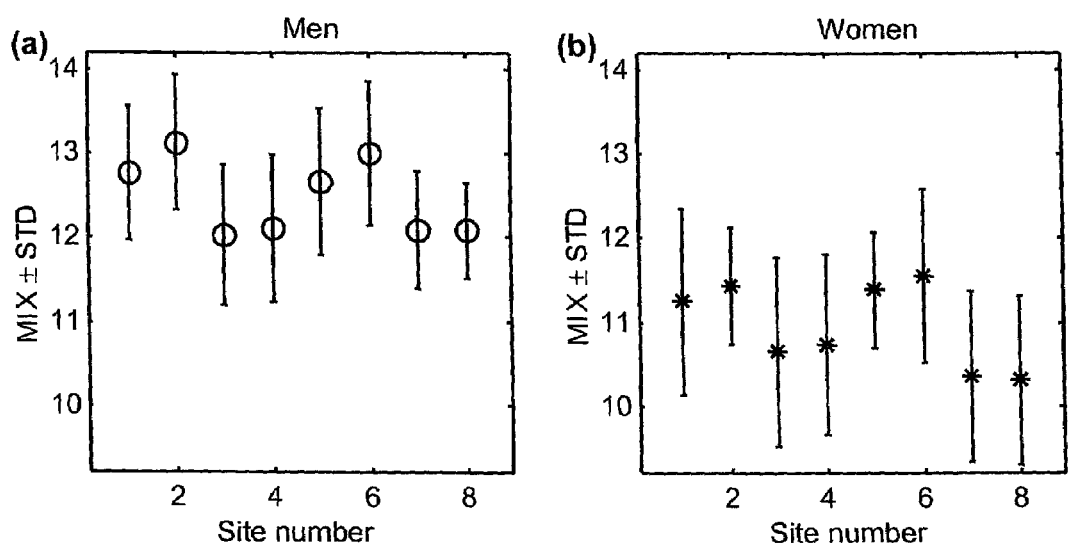
FIG. 4. Mean MIX ± standard deviation (STD) of depth setting number three for 15 men (a) and 12 women (b).

An example of the measured magnitude spectra is visualised in FIG. 3. MIX of the eight sites is visualised in FIG. 4. It can be seen that MIX of α direction varied systematically (i.e., MIX of the outer sites were higher than the inner). MIX for men were systematically higher than for women.

Figure 5:
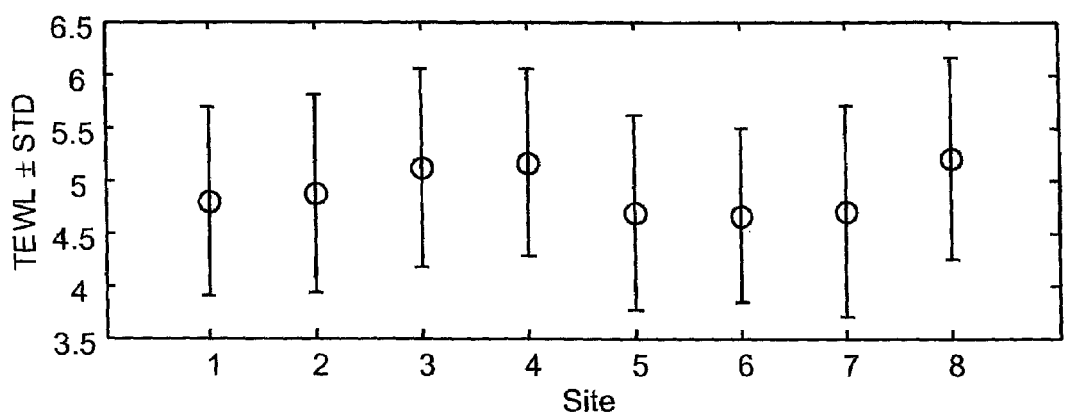
FIG. 5. Average TEWL ± standard deviation of the eight sites of 14 men and 13 women.

TEWL of the sites is visualised in FIG. 5. It can be seen that mean TEWL of the sites on the insides of the arms were higher than the outer sides, the α direction.

Three-Way Analysis of Variance of Magnitude Index and Trans Epidermal Water Loss Three-way ANOVA's were calculated for MIX, all depth settings, and for TEWL. Interactions between the directions were ignored. ANOVA tables are listed in Table 2 and Table 3. SS is the sum of squares, df the degrees of freedom. In ANAOVA, the total SS of the data is divided into SS of the responses and SS of the error (the variance not related to the responses). df is also separated into responses and error. MS is the mean squares, the SS for each degree of freedom. MS of the responses divided by MS of the error is called the F-ratio. Null hypothesis of ANOVA and MANOVA is that the F-ratio is equal or less than 1.0. The P-value is the probability that the null hypothesis is true, the likelihood that the data is noise. The significance levels used in this paper are $0.01<P<0.05$ (*), $0.001<P<0.01$ (), and $P<0.001$ (*).

TABLE 2

MANOVA table of the responses for MIX, depth setting number three.

| Direction | Error | | | Response | | | F | P | Significance |
|---|---|---|---|---|---|---|---|---|---|
| | SS | df | MS | SS | df | MS | | | |
| α | 9.7 | 26 | 0.37 | 38 | 1 | 38 | 103 | 0.000 | *** |
| β | 8.1 | 26 | 0.31 | 1.2 | 1 | 1.2 | 3.9 | 0.058 | ns |
| γ | 12 | 26 | 0.44 | 0.3 | 1 | 0.3 | 0.7 | 0.41 | ns |

TABLE 3

MANOVA of the responses measured with TEWL.

| Direction | Error | | | Response | | | F | P | Significance |
|---|---|---|---|---|---|---|---|---|---|
| | SS | df | MS | SS | df | MS | | | |
| α | 11.4 | 26 | 0.44 | 4.6 | 1 | 4.6 | 10.5 | 0.003 | ** |
| β | 11.1 | 26 | 0.43 | 1.3 | 1 | 1.3 | 3.0 | 0.097 | ns |
| γ | 11.6 | 26 | 0.45 | 1.6 | 1 | 1.6 | 3.5 | 0.071 | ns |

Significant differences were found for the α direction for both techniques ($P_{MIX}<0.001$ and $P_{TEWL}<0.01$). The β- and γ-directions were not significant. For MIX, the ANOVA of the different depth settings were almost identical. In order to save space, only depth setting number three is shown in Table 2. There were large individual differences between the patients (60–80% of the total variations), i.e. the biological variations were large.

Parallel Factor Analysis of Skin Impedance

Figure 6:
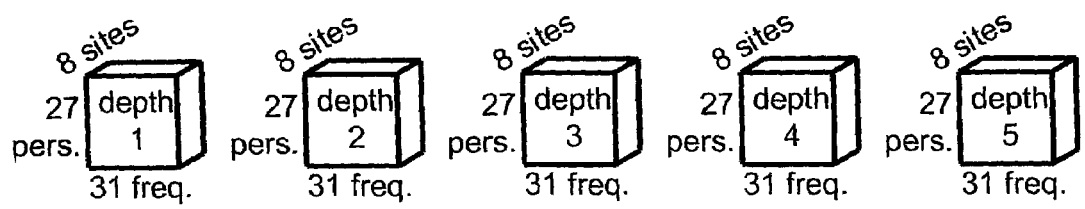
FIG. 6. Structure of the four-way raw magnitude data (27 persons×8sites×5 depth settings×31 frequencies).

The structure of the measured magnitude data was a four-way array (27×8×5×31) visualised in FIG. 6.

Mode 1: 27 persons

Mode 2: 8 sites

Mode 3: 5 depth settings

Mode 4: 31 frequencies

No good PARAFAC models were found using the raw magnitude data. Therefore the data were pre-processed using centering and scaling. Centering was performed column-wise across the actual modes, and scaling within the actual mode using the nprocess-algorithm in the N-way toolbox (26). The frequency mode was mean value centred and scaled to equal standard deviation. This pre-processing was made to normalise the exponential distribution of the data. Mode 2, the sites, was also centered. This was made in order to minimise the blocking effect of males and females, which seemed to destroy the multi-way structure of the data. Centering of the sites also reduced some of the biological noise, e.g. between-subject variations.

Figure 7:
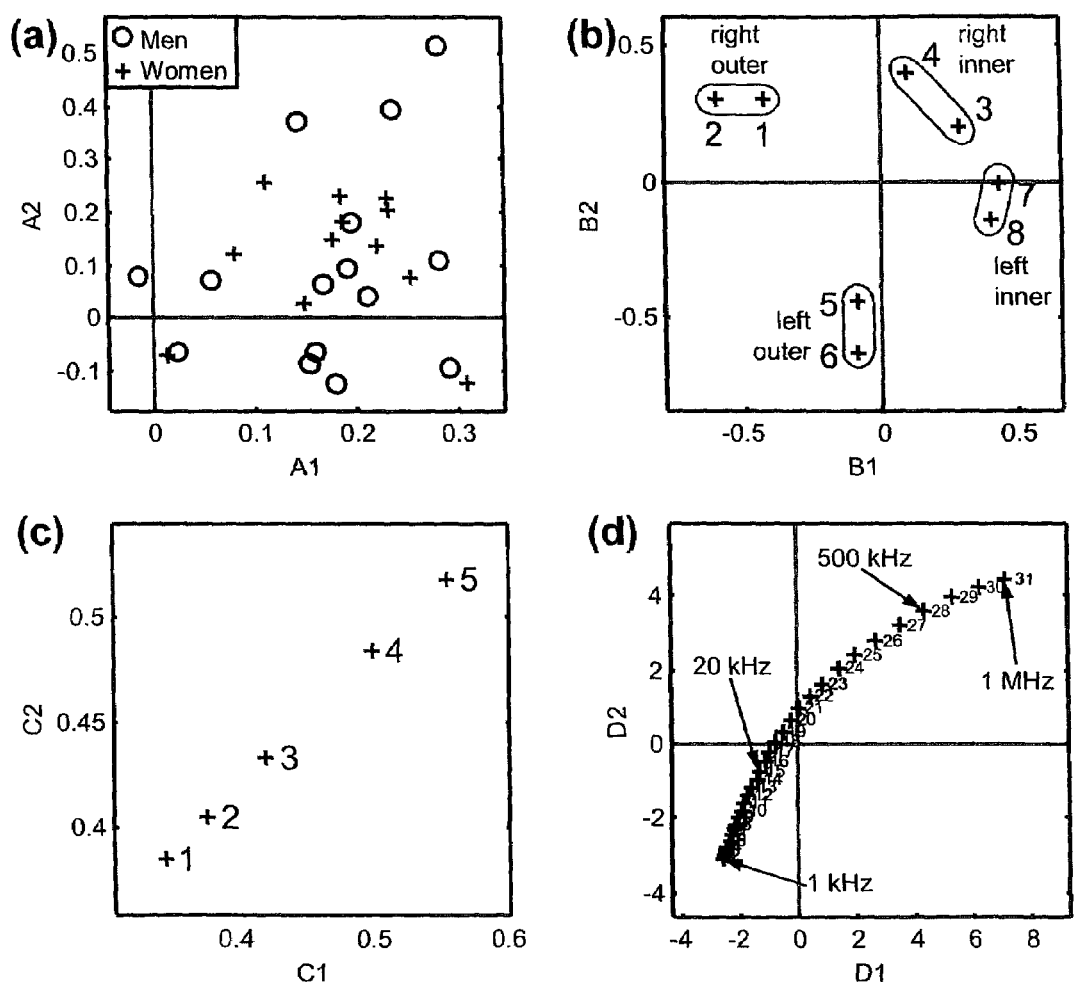
FIG. 7. Scatter plots of the loadings of the two PARAFAC components of mode 1–4: (a) persons, (b) site numbers, (c) depth settings, and (d) frequencies.

Two PARAFAC components were calculated. Extracting more PARAFAC components gave solutions difficult to interpret or degenerate solutions. The two-component PARAFAC model described 58.3% of the total variation, and it can once again be concluded that the data contained large individual variations. The sizes of the components are listed in Table 4. It should be noted that PARAFAC components are not necessarily orthogonal. Hence, the sums of squares of the components are not additive and will not sum up to the total sum of squares described by the model. The loadings of the four modes are visualised in FIG. 7.

Analysing the two loadings of mode 1 (scatter plot in FIG. 7a) it was found that there was no clear difference between males and females, though the women seem to have less spread than the men. There were no extreme readings or outliers.

TABLE 4

Sources of variation of the four-way PARAFAC model.

| Source of SS | % of total variation |
|---|---|
| PARAFAC model | 58.3 |
| Residual | 41.7 |
| Total | 100 |
| Component 1 | 37.3 |
| Component 2 | 27.5 |

Visual inspection of the loadings of mode 2 showed that $b_1$ described the difference between inner and outer side of the underarms (the α-direction). The second loading, $b_2$, described the difference between right and left arms (the γ-direction). No trend was found for the β-direction. The significance of the trends seen in FIG. 7a was tested using linear regression. Linear regressions were calculated for all combinations of loadings and arm directions ($b_1$ vs. α, $b_2$ vs. α, $b_1$ vs. β, ..., and $b_2$ vs. γ). It was found that there is a significant correlation between $b_1$ and α ($R^2$=0.73, P<0.01), and $b_2$ and γ ($R^2$=0.74, P<0.01), i.e. there is a clear connection between magnitude and arm location for the α- and γ-directions. No significant linear relations were found between the other combinations of loadings and directions ($R^2$<0.2, 0.2<P). It should be noted that linear relationship between the magnitude and direction is a rough approximation. Better fit would be expected if using more complicated regression models, e.g. multi-linear regression. But since the purpose of this test was to evaluate the significance of the relations between the parameters, and not to optimise the fit, the linear regression was sufficient.

Figure 8:
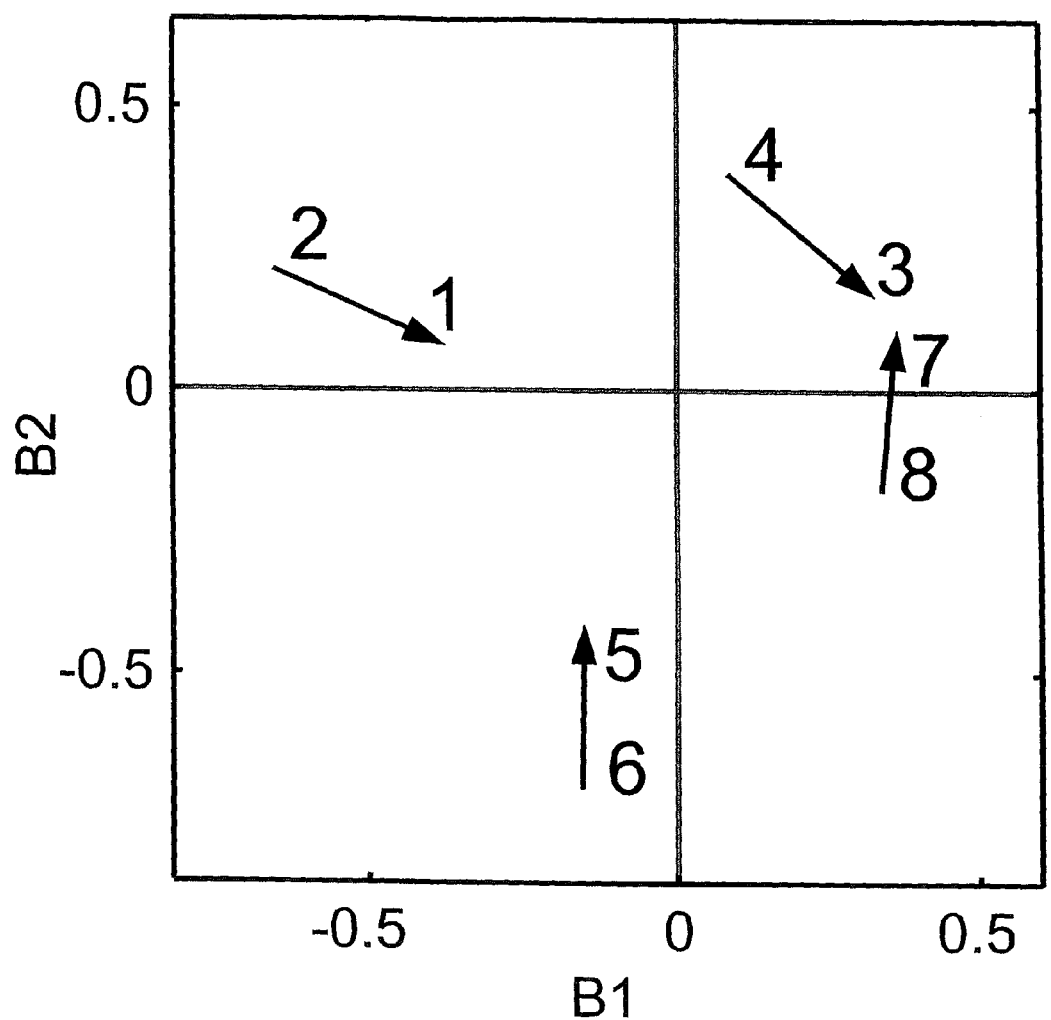
FIG. 8. Scatter plot of the two loadings of mode 2, the test sites, of the three-way PARAFAC model for depth setting number 1. The β-direction is marked with arrows.

As shown in FIG. 7c, the five depth settings of mode 3 were highly correlated, which is normal when measuring impedance of healthy skin with intact stratum corneum. This indicates that creating a three-way array (27×8×31) from a selected representative depth setting would give a simpler model without affecting the overall results. This was tested by calculating PARAFAC models for each depth setting of the pre-processed magnitude data. As expected, the three-way models all showed similar results as the four-way model. They described 57–60% of the variations of the three-way arrays, which is the same as the four-way PARAFAC model. Looking at the loadings of mode 2 of the three-way model for depth setting number one in FIG. 8, it can be seen that the overall trend is similar to the loadings the four-way model in FIG. 7b. Apart from the α and γ directions, there seems to a subtle relation between the impedance and the β direction. This trend faded with depth and there was no trend between impedance and beta direction present at depth setting number five.

The frequencies, shown in FIG. 7d, of mode 4 were highly correlated. Magnitude at high and low frequencies were the most important for the model, which implies that a new magnitude index, formulated from the two extreme frequencies 1 kHz and 1 MHz, would describe more of the variance of the data in this application than MIX, formulated from 20 and 500 kHz. The frequencies discussed are marked in FIG. 7d.

The two frequencies used in MIX were originally chosen to minimise the signal-to-noise levels of the skin impedance, taking into account both contact properties of the skin/electrode interface as well as engineering limitations, and to explain as much as possible of the magnitude. External noise can be a problem in some situations, specially for the phase angle, where the high frequencies can be noisy. During the clinical measurements of this experiment there were no interfering noise and the impedance signals were clean and smooth.

The first PARAFAC component was mainly affected by high frequencies around 1 MHz, and the second by high and low frequencies around 1 kHz and 1 MHz. This indicates that the magnitude in the α-direction is affected by the high frequencies, and the γ-direction by both high and low. I.e., magnitude of the inner side of the arm at 1 MHz is systematically higher than the outer side, and magnitude of the right arm is systematically higher at 1 MHz and lower at 1 kHz than the left arm. It must be noted that this is valid for the pre-processed data, not for the measured raw magnitude spectra.

The stability of the model was tested using leave-one-person-out technique. New models were calculated with one person excluded from the data. The new data were centred and scaled the same way as the data in the original model. One of the leave-one-person-out models was degenerate (a poor model) where the two components were highly correlated. The other 26 models, however, showed similar results as the original four-way model. This is an indication that the model is stable and reliable.

It has thus been shown that there are significant differences between outer and inner sides of arms. This was shown using two independent non-invasive measuring techniques, TEWL and skin impedance, and two different numerical approaches, classical statistics of TEWL and parameterised impedance, and PARAFAC of full impedance spectra. Differences between right and left arms were found for full impedance spectra analysed with PARAFAC.

No TEWL difference was found between the upper and the lower sites. This is consistent with the results presented by Rodrigues and Pereira (5), who found that TEWL around the centre of the volar forearms is relatively constant in the longitudinal direction. For the multi-frequency skin impedance however, a subtle relation between the magnitude and the longitudinal direction was found for depth setting number one.

It is not clear why no difference between the arms was found for TEWL even though it has been reported in the literature that these differences exist (5). Nevertheless, differences between right and left arms were found for the impedance. This indicates that the impedance technique is more precise than TEWL, at least in this example. The advantage of impedance over TEWL has previously been shown for several applications, specially in quantifying skin irritations (25).

The limited number of sites used in these experiments is not sufficient for a complete mapping of the properties of the volar forearms, especially not in the longitudinal direction, where only 40–50 mm of the total length of the arms was investigated. In order to map the total area of the volar forearms, at least 5 sites in the longitudinal direction, and 3 sites between the inner and outer sides of the arms would be required.

It is also not obvious how to analyze complex valued data using projection methods since the algorithms are normally made for real values. One approach is to transform the complex data to magnitude, phase angles, real part, and/or the imaginary part (23, 24, 27). This is not optimal because the number of variables in the non-complex data will be at least twice as many as in the complex data if all features of the complex data are included. Bro et al. (28) have made a PARAFAC algorithm for complex valued three-way arrays. Since the distribution of the data in this paper was exponential, and it is not clear how to pre-treat complex data, the PARAFAC algorithm for complex data was not used. Instead, several transformations of the complex data were analyzed. The solutions of the PARAFAC models of the different transformations all showed similar trends. In order to save space, only the PARAFAC model of the magnitude spectra is demonstrated in this paper. Tucker3 was also tested on the data and showed similar results as the PARAFAC models. Hence, considering the positive results of the leave-one-person out test and that similar results were found using two different projection methods, the model shown here is considered stable.

The data presented here are baselines, or reference readings, of a more detailed optimizing studies. When measuring these baselines, the measurement order was not completely random and the test sites were not located with high precision. This is not optimal experimental design, but it is believed not to affect the results shown here, and it could explain some of the large individual differences. Apart from the variations shown in this paper, there are also large within subject variations due to season, overall skin condition, skin temperature, and so on, and between subject variations due to sex, age, skin color, etc (29–31).

Within the relatively local area, such as the volar forearm, which is frequently used in skin research and dermatology testing, the skin property variations are surprisingly big. This implies that most care in the study design must be enforced in order to facilitate observations of subtle reactions. To prevent the variability of the skin properties of volar forearm not to overshadow the dermal responses in skin testing, proper experimental design has to be used, e.g. randomisation, differential measurements, and repeated measures (replicates), and reference sites should be carefully located contralaterally or ipcilaterally, but following the same site in time is obviously optimal. As demonstrated in this work, any ipcilateral reference reading should be chosen longitudinally.

Effect of Site on Glucose Level Measurements

Two persons (A and B) drank 100 g glucose dissolved in water on empty stomachs. The blood glucose concentration was followed in time by a common glucose meter. In parallel, skin impedance was collected using the Scibase II device.

Figure 9:
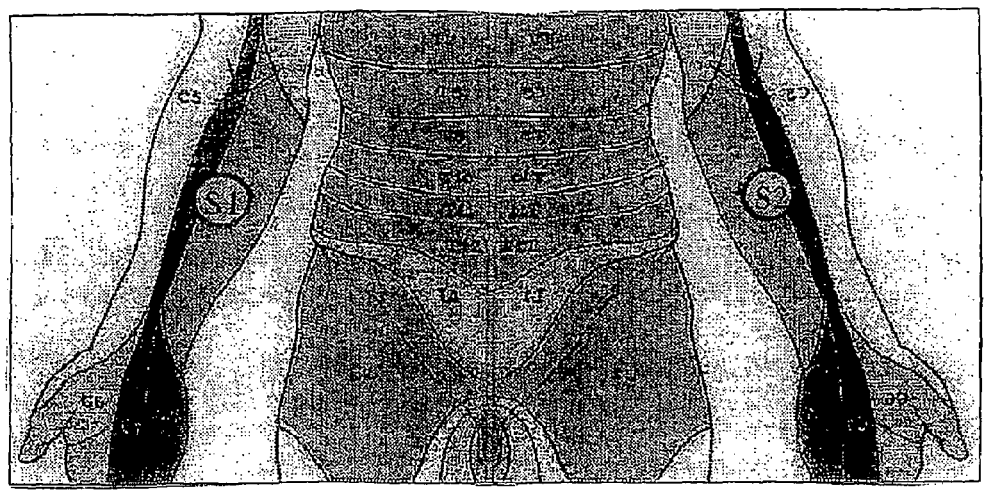
FIG. 9. Locations of two sites, S1, S2, where the skin impedance was measured for comparison with directly measured blood glucose levels.

Skin impedance was collected from two sites, on the left and right forearm as indicated in FIG. 9. Two sites were used in order to reduce inundation effects. The sites were carefully marked with a pen. Every second reading was measured on the left and right side. Blood glucose was collected from the fingertip of the actual arm. Blood glucose and skin impedance were measured for approximately two hours during increase and decrease of the blood glucose. The sites were cleaned using three tape strips per site before the impedance measurements. were taken.

Data Analysis

The skin impedance of the two test persons were visualised using principal component analysis (PCA) and correlation between blood glucose and skin impedance was modeled using partial least-squares regression (PLS). All calculations were made using the Simca-P software by Umetrics AB, Umeå, Sweden.

Results

Figure 10A:
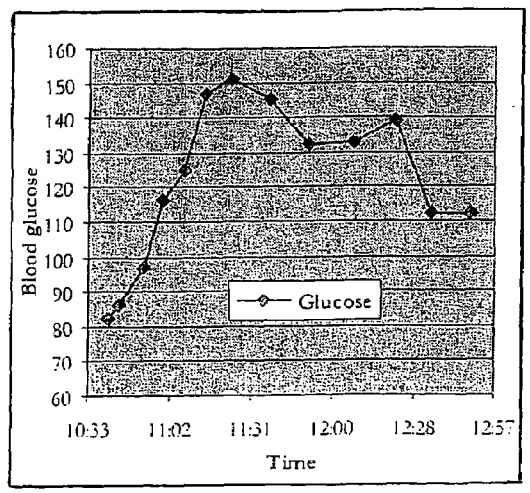
FIG. 10a. Graphical depiction of blood glucose level of Person A, as directly measured, over time.
Figure 10B:
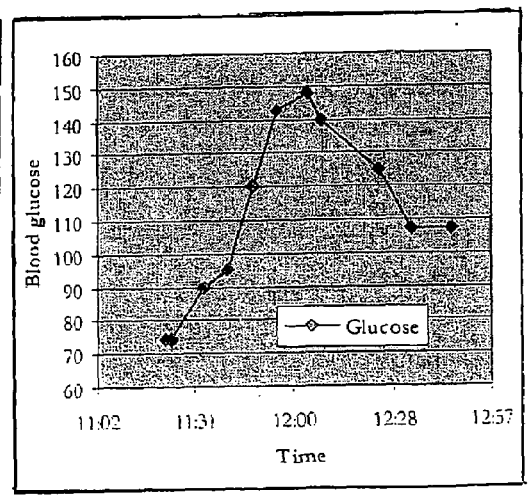
FIG. 10b. Graphical depiction of blood glucose level of Person A, as directly measured, over time.

The blood glucose levels of Persons A and B are listed in Table 5 and graphed in FIGS. 10a and 10b.

TABLE 5

Results of Blood Glucose Levels

| | Person A | | | | Person B | | |
|---|---|---|---|---|---|---|---|
| No. | Arm | Time | Glucose | No. | Arm | Time | Glucose |
| 1 | R | 10:41 | 82 | 1 | L | 11:22 | 74 |
| 2 | L | 10:44 | 86 | 2 | R | 11:24 | 74 |
| 3 | R | 10:53 | 97 | 3 | L | 11:34 | 90 |
| 4 | L | 10:59 | 116 | 4 | R | 11:41 | 95 |
| 5 | R | 11:07 | 125 | 5 | L | 11:48 | 120 |
| 6 | L | 11:14 | 147 | 6 | R | 11:55 | 143 |
| 7 | R | 11:24 | 151 | 7 | L | 12:04 | 148 |
| 8 | R | 11:38 | 145 | 8 | R | 12:08 | 140 |
| 9 | L | 11:51 | 132 | 9 | L | 12:25 | 125 |
| 10 | R | 12:07 | 133 | 10 | R | 12:34 | 107 |
| 11 | L | 12:22 | 139 | 11 | L | 12:46 | 107 |
| 12 | R | 12:35 | 112 | | | | |
| 13 | L | 12:49 | 112 | | | | |

The results obtained here thus establish the feasibility of improving the utility of impedance measurements for blood glucose determination by proper selection of the site at which impedance measurements are made, and by utilizing the same site from measurement to measurement.

Figure 13:
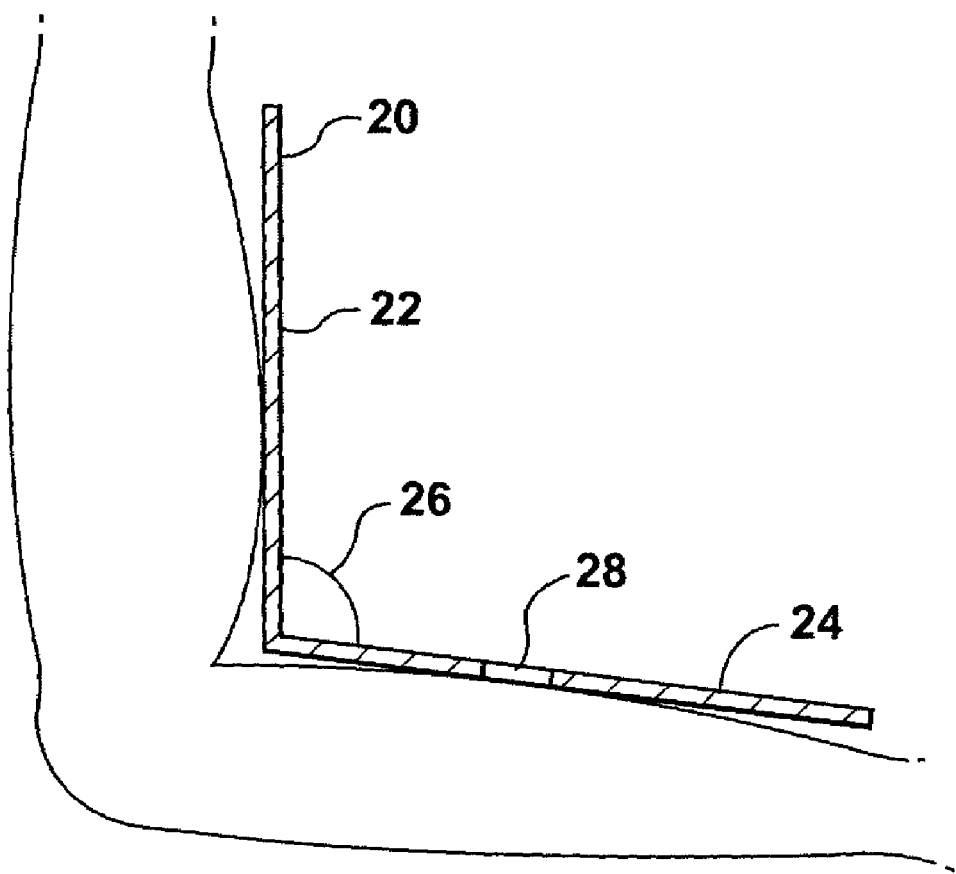
FIG. 13. Illustration, in section, of an apparatus for locating a site for measuring impedance on the volar forearm of a subject.

An apparatus 20 for use in selecting the site and ensuring that the same site is selected from measurement to measurement is illustrated in FIG. 13. The apparatus is of a relatively rigid material, e.g. a plastic, and is shaped to fit in the crook of an elbow formed when a subject bends his or her arm, the degree to which bending occurs being limited by the device. The device thus includes two extending flanges 22, 24 at a fixed angle 26 with respect to each other. In this way the location of the device is positively locatable with respect to the forearm for each measurement so that a probe can be located at the same site from measurement to measurement. The device may also present concave surfaces (when viewed from the lower left of FIG. 13) so as to receive therewithin and positively locate the device transverse of the lengthwise path of the arm. The device includes aperture 28 located in flange 24 to provide an opening which acts as an indicator for locating the probe against the arm at the same site on the skin of the subject from measurement to measurement. Alternatives to the illustrated device are possible. A device could devised for locating a probe against a different part of the body. The flanges of the illustrated device could be further modified by shaping the surfaces that abut skin surfaces of the subject to more closely engage the skin surfaces, rather than being simply straight in the lengthwise direction of the arm, as illustrated.

Multiple Treatment and Impedance Measurements

Another possible procedure which may be used to improve the reliability of impedance measurements in determining blood glucose levels involves a "stepped-indundation" procedure described below. This procedure involves wetting the site at which the impedance measurement is to be taken (i.e., the skin site with which the electrode is to placed in direct physical contact) a plurality of times for specifically defined periods of time, clearing the site after each exposure and measuring impedance after each clearing step. Once a satisfactory impedance reading is obtained, according to pre-determined criteria, the blood glucose level is determined.

In a specific embodiment, the apparatus used in these procedures is described in international patent application No. PCT/SE 91/00703, published under WO 92/06634 on Apr. 30, 1992. The apparatus is known in the marketplace as the SciBAse II depth selective spectrometer, and may be obtained from Sci.Base AB of Huddinge, Sweden. A conventional concentric probe was used for these tests.

The following inundation procedure was used with a conventional probe. Gauze inundation pads are kept in a closed beaker of 0.9% saline or packaged in a saturated state. The skin was inundated by holding the gauze pad in place at the test site for 40 seconds and then wiping any excess solution away before the impedance test, with inundation again for another 10 seconds, and wiping away any excess solution before the second impedance test. This procedure was repeated until a total of 70 seconds of inundation was reached, that is, for a total four impedance measurements were taken.

Figure 14:
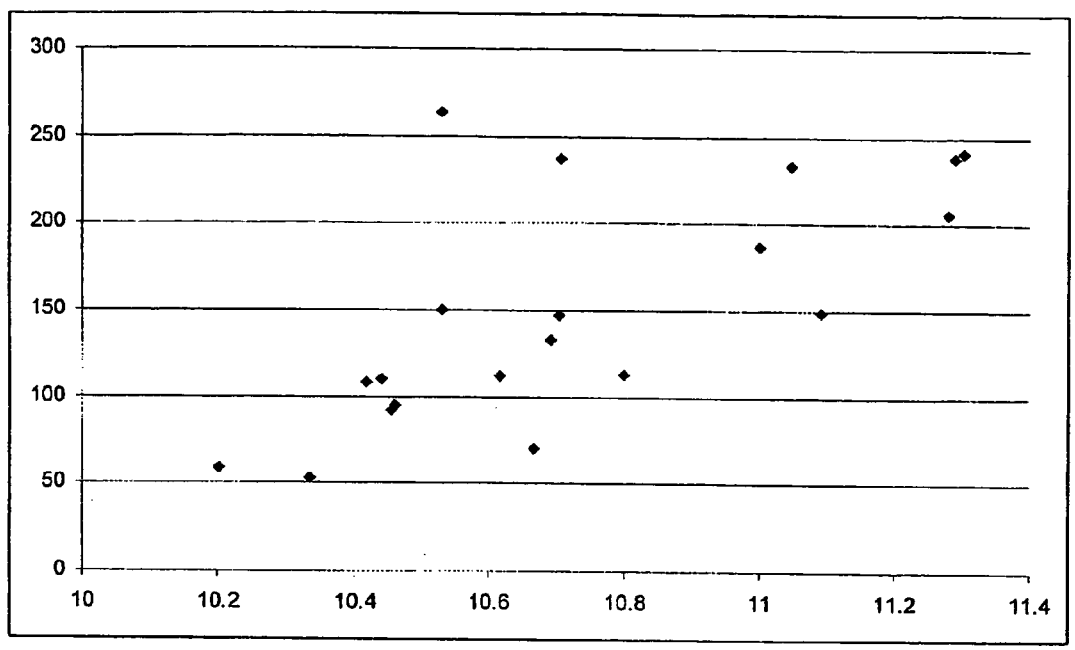
FIG. 14. Plot of blood glucose values measured directly versus values obtained from impedance measurements taken after stepped inundation of the site of electrode placement.

In a feasibility test, impedance and directly measured blood glucose data obtained for a subject over a period of three weeks were analyzed for an acceptable correlation. Directly measured glucose levels were obtained using a Glucometer Elite for each complete set of inundation-impedance measurement cycles (available from Elite Glucometer, Miles Canada, Diagnostics Division, Division of Bayer). Data were considered satisfactory if at 1 Mhz at depth 1 the kOhms value is within the range 1.25–1.45. Additional frequencies can be used. A preferred procedure for determining blood glucose is disclosed in U.S. Pat. No. 6,517,482. In the feasibility test for the inundation procedure, if more than one impedance test was within the pre-selected range, the kOhm value closest to 1.3 was selected. If the kOhm value was in range and IMIX at depth one value was between 10.2 and 11.5 then this IMIX value was accepted. Corresponding blood glucose levels were again measured directly using the Glucometer Elite device. Results obtained over several days are shown in FIG. 14. The indundation-measurement procedure can be followed for as few as two cycles, provided acceptable results are obtained in the second cycle. Otherwise three, or the four cycles described should be carried out.

The results shown in FIG. 14 establish the feasibility of improving the reliability of glucose levels as determined over an extended period of time using a given procedure involving impedance measuring impedance.

All references cited herein are incorporated into this specification in their entirety as though reproduced herein.

The scope of protection sought for any invention described herein is defined by the claims which follow. It will be appreciated by those skilled in the art that a variety of possible combinations and subcombinations of the various elements described herein exist, and all of these combinations and subcombinations should be considered to be within the inventor's contemplation though not explicitly enumerated here. This is also true of the variety of aspects of the processes and the combinations and subcombinations of elements thereof.

REFERENCES

All documents cited herein are incorporated into this specification by reference as though their contents were reproduced herein in their entirety.

1. Björnberg A. Skin reactions to primary irritants in patients with hand eczema: an investigation with matched controls. Thesis. Sahlgrenska Sjukhuset, Gothenburg, Sweden, 1968.
2. Nicander I, Norlén L, Brockstedt U, Lundh Rozell B, Forslind B, Ollmar S. Electrical impedance and other physical parameters as related to lipid content of human stratum corneum. Skin Res Technol 1998: 4: 213–221.
3. Nilsson G E. On the measurement of evaporative water loss. Methods and clinical applications. Thesis. Linköping Medical University, Linköping, Sweden, 1977.
4. Pinnagoda J, Tupker R A, Agner T, Serup J. Guidelines for transepidermal water loss (TEWL) measurement; A report from the Standardization Group of the European Society of Contact Dermatitis. Contact Dermatitis 1990: 22: 164–178.
5. Rodrigues L, Pereira L M. Basal transepidermal water loss: right/left forearm difference and motoric dominance. Skin Res Technol 1998: 4: 135–137.
6. Van der Valk P G, Maibach H I. Potential for irritation increases from the wrist to the cubital fossa. Br J Dermatol 1989 Dec: 121 (6): 709–12.
7. Tur E, Maibach H I, Guy R H. Spatial variability of vasodilatation in human forearm skin. Br J Dermatol. 1985 Aug: 113(2): 197–203.
8. Jackson J. A User's Guide to Principal Components. New York: Wiley, 1991.
9. Mardia V, Kent J, Bibby J. Multivariate Analysis. London: Academic Press, 1979.
10. Wold S, Esbensen K, Geladi P. Principal component analysis. Chemometrics Intell. Lab. Syst. 1987: 2: 37–52.
11. Geladi P, Åberg P. Three-way modelling of a batch organic synthesis process monitored by near infrared spectroscopy. J Near Infrared Spectrosc 2001: 9: 1–9.
12. Bro R. PARAFAC: Tutorial and applications. Chemometrics Intell. Lab. Syst. 1997: 38: 149–171.
13. Harshman R A. Foundations of the PARAFAC procedure: Model and conditions for an 'explanatory' multimode factor analysis. UCLA Working Papers in phonetics 1970: 16: 1–84.
14. Carrol J D, Chang J. Analysis of individual differences in multidimensional scaling via an N-way generalization of the Eckart-Young decomposition. Psychometrika 1970: 35: 283–319.
15. Geladi P. Analysis of multi-way (multi-mode) data. Chemometrics Intell. Lab. Syst. 1989: 7: 11–30.
16. Smilde A. Three-way analyses. Problems and prospects. Chemometrics Intell. Lab. Syst. 1992: 15: 143–157.
17. Coppi R, Bolasco S. eds. Multiway Data Analysis. Amsterdam: Elsevier, 1989.
18. Andersson C, Bro R. eds. Special Issue, Multiway Analysis. J. Chemometrics 2000: 14.
19. Foster K, Schwan H. Dielectric properties of tissues and biological materials: a critical review. Crit. Rev. Biomed. Eng. 1989: 17: 25–104.
20. Ollmar S, Nicander I. Information in multi frequency measurement of intact skin. Innov Tech Biol Med 1995: 16: 745–751.
21. Ollmar S. Making electronic biopsies into a viable future for non-invasive diagnostics with electrical impedance. Med Biol Eng Comp 1999: 37, Suppl 2: 116–117.
22. Ollmar S. Methods of information extraction from impedance spectra of biological tissue, in particular skin and oral mucosa—a critical review and suggestions for the future. Bioelectrochemistry & Bioenergetics 1998: 45: 157–160.
23. Åberg P, Nicander I, Geladi P, Ollmar S. Multivariate regression model of normal and chemically irritated skin shows predictive ability. Proc. EMBC 2001, Istanbul, Turkey, Oct. 25–28, 2001, ISBN 0-7803-7213-1.
24. Lindholm-Sethson B, Han S, Ollmar S, Nicander I, Jonsson G, Lithner F, Bertheim U, Geladi P. Multivariate analysis of skin impedance data in long-term type 1 diabetic patients. Chemometrics Intell. Lab. Syst. 1998: 44: 381–394.

25. Nicander I. Electrical impedance related to experimentally induced changes of human skin and oral mucosa. Thesis. Karolinska Institutet, Stockholm, Sweden, 1998.
26. Andersson C, Bro R. The N-way Toolbox for MATLAB. Chemometrics Intell. Lab. Syst. 2000: 52 (1): 1–4.
27. Lindholm-Sethson B, Geladi P, Nelson A. Interaction with a phospholipid monolayer on a mercury electrode. Multivariate analysis of impedance data. Analytica Chimica Acta 2001: 446: 121–131.
28. Bro R, Sidiropoulos N D, Giannakis G B. A Fast Least Squares Algorithm for Separating Trilinear Mixtures. Proc. ICA99—Int. Workshop on Independent Component Analysis and Blind Signal Separation, Jan. 11–15, Aussois, France: 289–294, 1999.
29. Cornish B H, Thomas B J, Ward L C. Effect of temperature and sweating on bioimpedance measurements. Appl Radiat Isot 1998 May-June: 49(5–6): 475–6.
30. Nicander I, Ollmar S. Electrical impedance measurements at different skin sites related to seasonal variations. Skin Res Technol 2000: 6: 81–86.
31. Robinson MK. Intra-individual variations in acute and cumulative skin irritation responses. Contact Dermatitis. 2001 August: 45(2): 75–83.

What is claimed is:

1. A method for non-invasively monitoring a component in a body fluid of a subject, the method comprising:
   (i) exposing a skin site of the subject at which a measurement is to be made to an aqueous salt solution for a pre-determined first period of time;
   (ii) (a) removing excess of the solution from the site; (b) measuring impedance at the site;
   (iii) exposing the site to the solution for a pre-determined second period of time and repeating step (ii);
   (iv) determining whether the impedance measured in step (iii) falls within a pre-determined range;
   (v) repeating steps (iii) and (iv) as necessary until the impedance measured in step (iii) falls within the pre-determined range; and
   (vi) determining the amount of the component in the fluid based upon the impedance measured in step (v).

2. The method of claim 1, wherein the range of step (iv) is empirically determined for the subject, the empirical determination being based on impedance measurements and a second type of measurement in which the amount of component present is determined for a sample of the body fluid obtained from the subject.

3. The method of claim 2, wherein steps (iii) and (iv) are repeated at least until the impedance measured in step (iii) falls with said range for two consecutive of the impedance measurements.

4. The method of claim 3, wherein determining the amount of the component is based on an average of the at least two consecutive impedance measurements.

5. The method of claim 4, wherein the first period is greater than said second period.

6. The method of claim 5, wherein the first period is at least about 40 seconds.

7. The method of claim 6, wherein the second period is less than about 20 seconds.

8. The method of claim 7, wherein the second period is less than about 15 seconds.

9. The method of claim 8, wherein the second period is about 10 seconds.

10. The method of claim 9, wherein the first period is less than about 60 seconds.

11. The method of claim 10, wherein the first period is less than about 50 seconds.

12. The method of claim 11, wherein the first period is about 40 seconds.

13. The method of claim 12, wherein the body fluid ii blood.

14. The method of claim 13, wherein the component is glucose.

15. The method of claim 14, wherein the aqueous salt solution comprises an inorganic salt compatible with human skin.

16. The method of claim 15, wherein the aqueous solution is a saline solution.

17. The method of claim 16, wherein, in step (ii) (b), measuring skin impedance includes abutting an electrode in direct contact with the skin site and/or the impedance is measured a plurality of frequencies.

* * * * *